(12) United States Patent
Colombo et al.

(10) Patent No.: US 10,195,034 B2
(45) Date of Patent: Feb. 5, 2019

(54) SYSTEMS AND METHODS FOR MAGNETIC INDUCTION OF A PENILE PROSTHESIS

(71) Applicant: Board of Trustees of the Southern Illinois University, Springfield, IL (US)

(72) Inventors: Alberto Colombo, Springfield, IL (US); Kevin McVary, Springfield, IL (US); Brian Le, Madison, WI (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 73 days.

(21) Appl. No.: 15/357,793

(22) Filed: Nov. 21, 2016

(65) Prior Publication Data

US 2017/0143491 A1    May 25, 2017

Related U.S. Application Data

(60) Provisional application No. 62/258,228, filed on Nov. 20, 2015.

(51) Int. Cl.
| | | |
|---|---|---|
| *A61F 2/26* | (2006.01) | |
| *H05B 6/10* | (2006.01) | |
| *A61B 5/1455* | (2006.01) | |

(52) U.S. Cl.
CPC ............... *A61F 2/26* (2013.01); *H05B 6/10* (2013.01); *A61B 5/14551* (2013.01)

(58) Field of Classification Search
CPC .... A61F 2/26; A61F 2210/0023; A61L 27/06; A61L 27/50; A61L 2400/16

USPC ..................................................... 600/38–41
See application file for complete search history.

(56) References Cited

U.S. PATENT DOCUMENTS

| | | | |
|---|---|---|---|
| 6,563,096 B1 | 5/2003 | Pacholok et al. | |
| 6,710,314 B2 | 3/2004 | Reiss et al. | |
| 7,335,156 B2 * | 2/2008 | Pattern .................... | A61N 1/40 600/14 |
| 2001/0031906 A1 * | 10/2001 | Ishikawa ................ | A61N 2/008 600/13 |
| 2011/0251687 A1 * | 10/2011 | Prescott ................... | A61F 2/18 623/10 |
| 2011/0301402 A1 * | 12/2011 | Xu .......................... | A61N 2/006 600/14 |
| 2013/0131443 A1 * | 5/2013 | Le ............................ | A61F 2/26 600/40 |

* cited by examiner

*Primary Examiner* — Samuel Gilbert
(74) *Attorney, Agent, or Firm* — Polsinelli PC

(57) ABSTRACT

Systems and methods for magnetic induction of a penile prosthesis are disclosed. The magnetic induction system includes a wand that has a coil arrangement covered with a thermal and electrical insulator sheath operable to generate an alternating magnetic field. The coil arrangement of the sheath is configured to receive the length of the penile prosthesis therein. The penile prosthesis may be made from a shape memory material such that application of alternating magnetic fields generated by the magnetic induction system induces eddy currents that raise the temperature of the penile prosthesis to a temperature above the austenitic transformation temperature that allows the penile prosthesis to achieve an erect state.

14 Claims, 10 Drawing Sheets

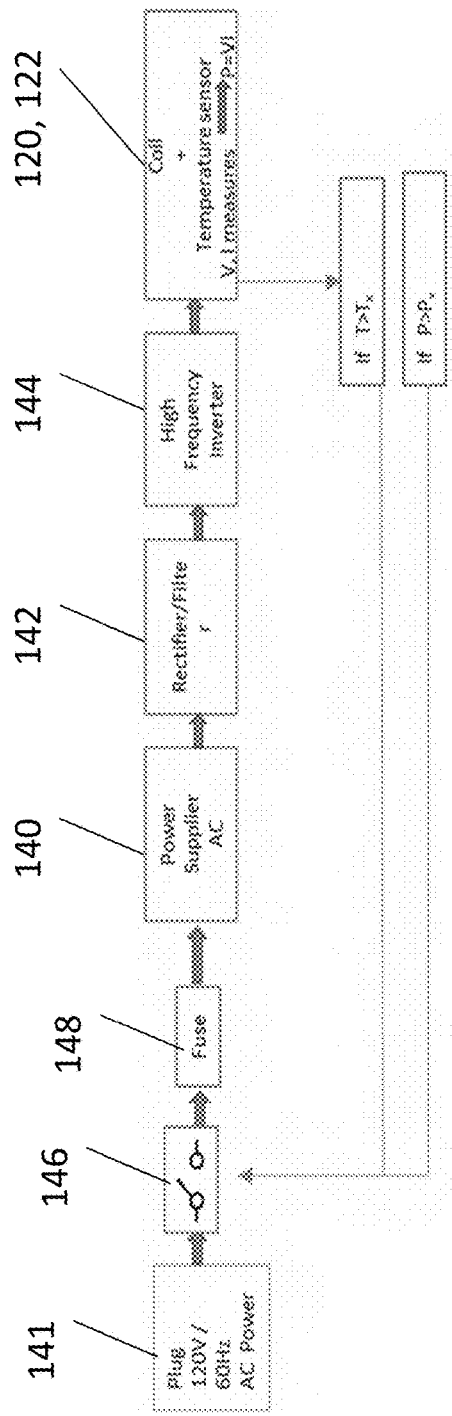
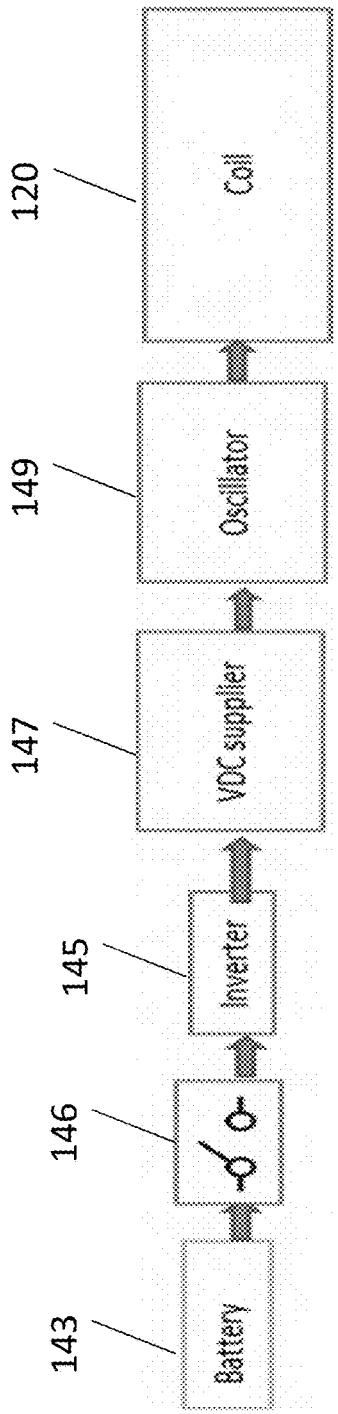
FIG. 2B
FIG. 2C

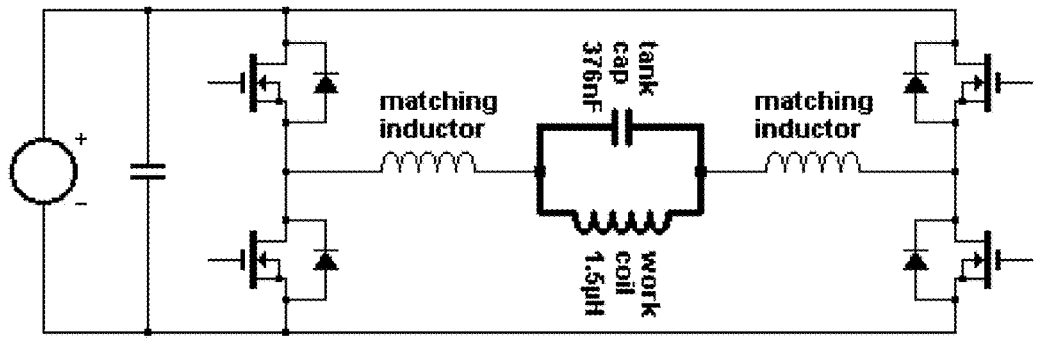
FIG. 2D
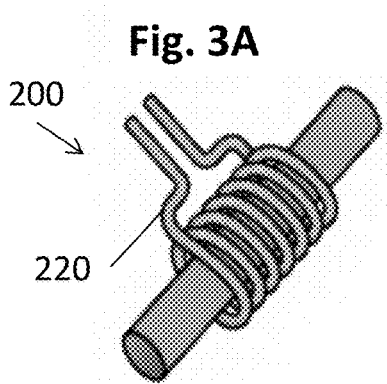
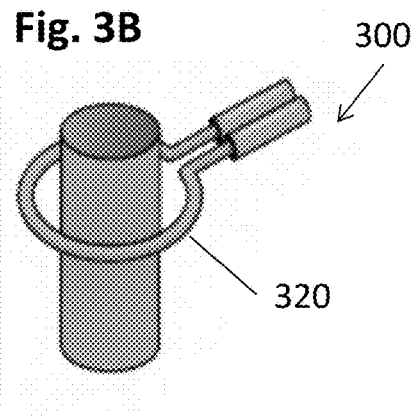
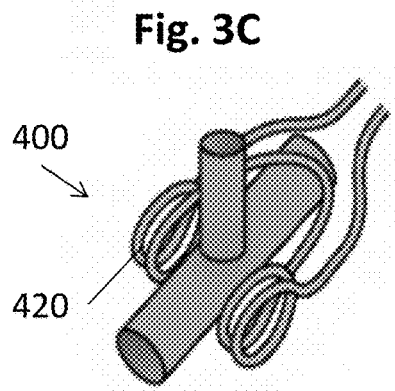
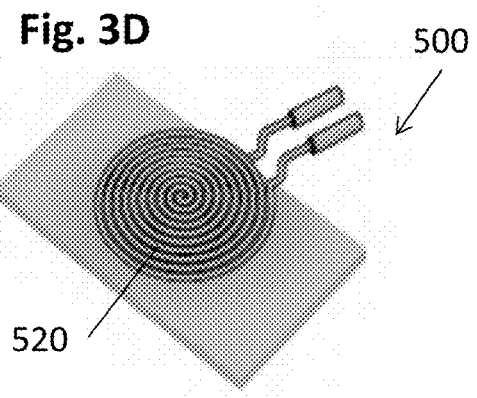

SYSTEMS AND METHODS FOR MAGNETIC INDUCTION OF A PENILE PROSTHESIS

CROSS REFERENCE TO RELATED APPLICATIONS

This is a non-provisional application that claims benefit to U.S. provisional application Ser. No. 62/258,228 filed on Nov. 20, 2015, which is incorporated by reference in its entirety.

FIELD

The present disclosure relates to a magnetic induction apparatus and in particular to methods and systems for magnetic induction of a penile prosthesis using the magnetic induction apparatus.

BACKGROUND

Erectile dysfunction (ED) is a multifactorial disease that affects approximately 30 million American men and is continuing to increase along with the upsurge in diabetes, hypertension and cardiovascular disease. When first line and second line medications such as the phosphodiesterase 5 inhibitor class of medications or direct injections fail, surgical implantation of penile prostheses offers a permanent solution. Surgical implantation of prostheses is a known practical means of treating erectile dysfunction.

Two broad classes of penile prostheses are typically used, the inflatable prosthesis and the semi-rigid prosthesis. The inflatable penile prosthesis aims to closely parallel a natural erection by shifting fluid from one area of the device, usually a reservoir, to the cylinders within the corpora cavernosa under hydraulic pressure to mimic the erect state. It relies on a closed system of reservoirs, pumps, valves and hydraulic pressure to produce a simulated erection sufficient for coitus. Consequently, the surgical implantation of this device is more complex and is prone to mechanical failure. Indeed only 67 to 88% of such devices are fully functional after 10 years. The advantages of the inflatable prosthesis are that it appears more physiologic and does not exert constant pressure on surrounding tissues when in the flaccid state, thereby reducing the risk of erosion.

In contrast, the semi-rigid prosthesis strikes a balance between being rigid enough for penetration, but malleable enough to allow positioning of the prosthesis downwards when not in use. The advantages of a semi-rigid prosthesis are that the device is simple, reliable, involves a smaller dissection, has fewer parts, and requires minimal dexterity to use. The disadvantages are that the prosthesis appears constantly erect, exerts more force on the surrounding tissues, and has an increased risk for erosion.

A solution to these previous penile implants is a penile prosthesis that is implantable in the corpus cavernosum. The penile prosthesis has a cylindrical outer contour along its longitudinal axis, is comprised of a shape memory alloy, and has a dimension that enlarges in response to an increase in temperature around the penile prosthesis. A useful memory alloy would be a Nitinol-Titanium (or Ni—Ti or referred to as Nitinol) alloy that undergoes a transition from a more malleable martensitic state to a more rigid austenitic state with application of heat. Heat can be provided in different ways, however, in a romantic environment, few options are available that can ruin the mood of the moment. Such means of providing heat to the penile prosthesis can include getting a wash rag wet with warm water and applying it to the penis or heating a hot pad in a microwave and applying it to the penis. Other issues related to heat transfer may cause the skin and other tissue around the penile prosthesis to burn in trying to get the memory alloy in the penile prosthesis to respond. Furthermore, the application of these means of heating may cause parts of the penile prosthesis to respond to heat but other parts of the penile prosthesis not to respond because the heat is not appropriately distributed.

Thus there is a need for a tool that induces heat upon a penile prosthesis that uses a shape memory alloy that is discrete, efficient and responsive. The tool should be appropriately sized so that it can be portable and reusable. There should also be a means to distribute the heat to the penile prosthesis in a more evenly distributed manner so that the memory alloy is heated in an even manner.

BRIEF SUMMARY OF THE INVENTION

Various embodiments of a magnetic induction apparatus and system having a magnetic induction apparatus for generating heat in a shape memory alloy penile prosthesis are disclosed. The magnetic induction apparatus may include a power source for generating a current and a coil operatively connected to the power source for receiving the current. The current in the coil produces an alternating magnetic field which induces eddy currents and generates heat in the penile prosthesis to change the penile prosthesis from a flaccid state to a rigid state.

The coil may be a multi-turn helical coil, a single-turn coil, a split helical coil, a pancake coil, or any other other coil form. The magnetic induction apparatus may further include a bore, such that the apparatus is configured as a sheath and the penile prosthesis is placed within the bore for heat transmission. In addition, the magnetic induction apparatus may be configured as a wand with a coil arrangement configured to cover a portion of the penile prosthesis such that the wand is moved back and forth motion along the penis to heat the penile prosthesis. The magnetic induction apparatus may also heat the penile prosthesis to a critical temperature, and the critical temperature may range between about 40° C. about 45° C. In some embodiments, the magnetic induction apparatus may further include a rectifier and/or a frequency inverter to produce the alternating magnetic field. In some embodiments, the current from the power source to the coil may be a low frequency AC current or a radio frequency (RF) current. In some embodiments, the magnetic induction apparatus may further include a thermal and electrical insulation cover made of silicon rubber, hypoxia, fiber glass, PTFE, or combinations thereof. The magnetic induction apparatus may further include a temperature sensor, a power sensor, or a pulse oximeter.

In another embodiment, the magnetic induction apparatus may include a power source for generating a current and a coil operatively connected to the power source for receiving the current such that the coil generates an alternating magnetic field which induces eddy currents and generates heat in the penile prosthesis to change the penile prosthesis from a flaccid state to an erect state through a change from martensitic to austenitic phase. In addition, the magnetic induction apparatus includes a bore wherein the apparatus is configured as a sheath and the penile prosthesis is placed within the channel of the bore for heating. The penile prosthesis may further include a conductive material selected from the group consisting of gold, silver, graphene, graphite, or high conductive non-ferromagnetic materials. The more conductive material may be plated directly on the exterior or interior of the penile prosthesis. In another embodiment, the shape memory alloy exoskeleton of the penile prosthesis may be surrounded by a conductive sheath which is able to increase the overall conductivity for the eddy currents.

In other embodiments, the disclosure herein provides for a method for activating a penile prosthesis in a touchless manner. The method may include providing a penile prosthesis comprising a shape memory alloy; providing a magnetic induction apparatus for inducing an alternating magnetic field to the penile prosthesis; generating eddy currents in the shape memory alloy exoskeleton of the penile prosthesis from the alternating magnetic field; and generating heat in the penile prosthesis caused by the eddy currents to change the penile prosthesis from a flaccid state to a rigid state. The magnetic induction apparatus may include a power source for generating a current and a coil operatively connected to the power source for receiving the current.

BRIEF DESCRIPTION OF THE DRAWINGS

FIG. 2B is a simplified block diagram of the magnetic induction apparatus in another embodiment, FIG. 2C is a simplified block diagram of the magnetic induction apparatus in another embodiment, and FIG. 2D is a circuit diagram of a full bridge induction heater, according to aspects of the present disclosure;

FIG. 3A is an illustration of a multi-turn helical coil, FIG. 3B is an illustration of a single-turn coil, FIG. 3C is an illustration of a split helical coil, and FIG. 3D is an illustration of a pancake coil, according to aspects of the present disclosure;

Corresponding reference characters indicate corresponding elements among the view of the drawings. The headings used in the figures do not limit the scope of the claims.

DETAILED DESCRIPTION

Figure 1:
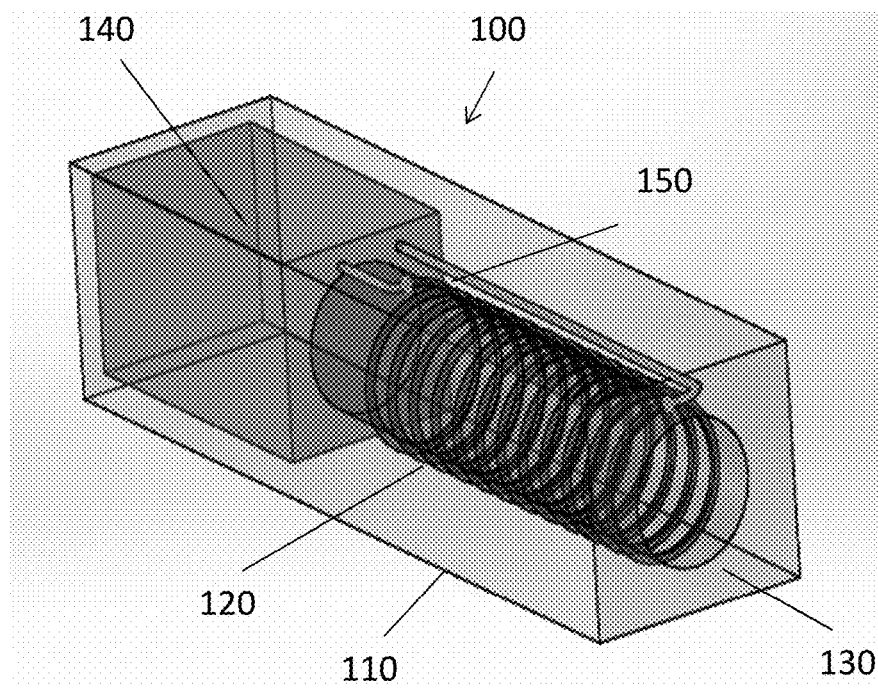
FIG. 1 is an isometric view of one embodiment of a magnetic induction apparatus having a sheath design, according to aspects of the present disclosure.

A novel magnetic induction system is provided to induce heat within a penile prosthesis by means of a magnetic induction apparatus. Magnetic induction takes advantage of a magnetic field generated by an electric current. One means to induce this magnetic field is to use a coil to create the magnetic field that transmits energy to the penile prosthesis. This energy creates an increase in the temperature up to the critical temperature of the penile prosthesis. The advantages of such a technique may be provided by an easy-to operate apparatus in the form of a sheath or "wand" or other device capable of creating a magnetic induction. It is important that the magnetic induction apparatus is regulated with the appropriate wattage to induce the correct amount of heat in a timely and useful fashion.

The present disclosure further relates to a novel method and apparatus for activating a penile prosthesis including a shape memory alloy in a touchless manner using electromagnetic induction as a method of transmitting energy without direct contact between the magnetic induction apparatus and the patient's groin area. Such a method has the goal to activate the penile prosthesis in an efficient and discrete way.

The use of a magnetic induction apparatus with a penile prosthesis made from a shape memory alloy circumvents many of the challenges associated with placement and manipulation of pumps and eliminates the need for a reservoir required in standard penile prostheses to provide a means for the penile prosthesis to assume an erect state from a flaccid state. The penile prostheses' silastic coverings do not affect activation. During activation, the penile prosthesis is able to produce enough force to straighten into an erect state and expand radially, creating girth against the tissues of the penis. The same technology may be used for activation of other Nitinol or other shape memory alloy (SMA) based medical devices.

U.S. Pat. No. 9,204,966 which is incorporated by reference in its entirety describes a novel penile prosthesis that uses shape memory alloys as a "molecular ratchet" to obtain a simulated erection. The novel penile prosthesis described in U.S. Pat. No. 9,204,966 can switch from a "flaccid"/martensitic phase to a "rigid"/austenitic phase with an increase in temperature. In an activation embodiment, heat can be applied in the groin area with the use of a warm pack. However, as noted above such a system can be unpractical and uneasy for some people.

The various embodiments of the magnetic induction apparatus use magnetic induction to activate the penile prosthesis in a more discrete way. The magnetic induction apparatus makes use of the principle of electromagnetism, where alternating magnetic fields induce eddy currents and generate heat in a conducting material. Furthermore, the same alternating magnetic field induces magnetic hysteresis, which occurs in magnetic materials and thereby generates heat. The Maxwell-Faraday equation (1) is a generalization of Faraday's law, which is a basic law of electromagnetism predicting how a magnetic field will interact with an electric circuit to produce an electromotive force (EMF).

$$\nabla \times E = -\frac{\partial B}{\partial t} \qquad (1)$$

A penile prosthesis may include an exoskeleton made from a shape memory alloy can be activated to the "erect and expanded phase" by increasing the temperature of the penile prosthesis to a critical temperature. Magnetic induction provides for a pump-free and touchless system of activation of the penile prosthesis. "Touchless" as used herein means that the magnetic induction apparatus may or may not come into contact with the penis at any point or for any period of time during the operation of the magnetic induction apparatus. In some embodiments, the magnetic induction apparatus may be an external activator device to the mammalian body which would apply energy to the penile prosthesis in order to increase its temperature above the austenitic transformation temperature or critical temperature such that the penile prosthesis assumes a rigid or semi-rigid state. In this embodiment, the magnetic induction apparatus would induce the creation of eddy currents on the shape memory alloy-based penile prosthesis generating an increase in temperature above a critical temperature of the shape memory alloy, thereby converting the penile prosthesis exoskeleton from martensitic to austenitic. In other embodiments, the shape memory alloy-based penile prosthesis may be modified to better adapt to the magnetic induction apparatus.

Figure 2A:
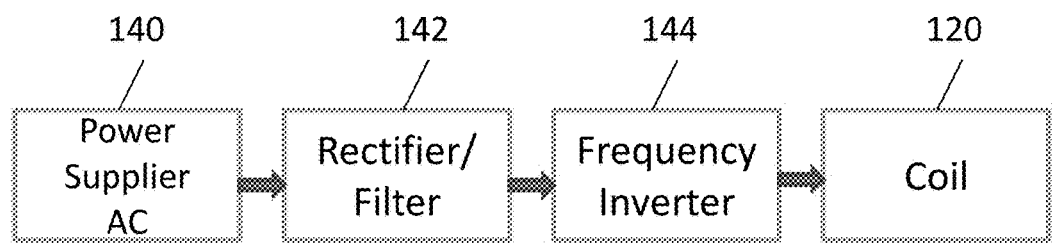
FIG. 2A is a simplified block diagram showing the current flow of the electric current from the power supply to the coil of the magnetic induction apparatus.

Referring to FIG. 1, in one embodiment, the magnetic induction apparatus, designated 100, may include a sheath 110 with a coil or series of coils 120 around a center bore 130. The coils 120 may be connected to a power source and circuitry 140 by wires 150. As illustrated in FIG. 2A, the power source 140 may be used to generate an AC current, which may then pass through a rectifier/filter 142 and/or a frequency inverter 144 before reaching the coil 120. FIG. 2B is a simplified block diagram of the magnetic induction apparatus 100 in another embodiment. In this embodiment, a 120 V/60 Hz plug 141 may provide AC power, which may be operatively connected to a switch 146, which may be operatively connected to a fuse 148. The fuse 148 may be operatively connected to the power source 140, such as an AC power supplier. The current may then flow to the rectifier/filter 142 and a high frequency inverter 144 before reaching the coil 120. A temperature sensor 122, such as a thermocouple or other temperature gauging system, may also be beside or incorporated with the coil 120 to measure the temperature and power at the coil 120. In another embodiment, a power sensor may also be used to calculate coil current and voltage and give the power at the coil 120. The temperature sensor 122 and/or the power sensor may act as a safety mechanism. If the temperature or power exceeds a predetermined threshold, the switch 146 will open to cut power to the magnetic induction apparatus 100. In another embodiment, the coil 120 could be associated with pressure sensors which may feel the expanding girth of the penis and open the on/off switch 146. In another embodiment, when the switch 146 is activated, a timer may be started which may run as long as the system is in function. The timer may open the on/off switch 146, arresting the magnetic field once a determined or threshold amount of time associated with a determined or threshold amount of delivered electromagnetic energy is passed.

In an embodiment, the magnetic induction apparatus may have a power supply 140 which may be used to engage the magnetic induction apparatus 100 to a source of AC current. A rectifier 142 can be used to convert AC power into DC power. The rectifier 142 may be combined with a filter to remove possible ripples due to the AC/DC conversion. A high frequency inverter 144 may follow to generate an AC current. A coil 120 is engaged to the high frequency inverter 144 to create a variable magnetic field on the shape memory alloy. The frequency inverter 144 may use or not a resonant circuit. The high frequency inverter 144 may have different structure such as a half-bridge, full bridge, push pull, or single ended variety. FIG. 2D shows a resonant full-bridge oscillator. The system can be activated by a switch 146. A fuse 148 may be added to the system as a safety system to avoid possible current overcharges. Voltage and current may be measured in the coil 120 and temperature may be measured in the coil surface or nearby it, including the airspace between the penis and the coil or on the penis surface. If temperature, voltage, current, or power reach a critical value, a signal may switch off the magnetic induction apparatus 100 as a further safety measure.

In another embodiment the device may be battery operated as shown in FIG. 2C. In some embodiments, a battery 143 may be operatively connected to a switch 146, which may be operatively connected to an inverter 145, which may be operatively connected to a power source 140, such as a DC voltage supplier (VDC) 147. The current may then flow through an oscillator 149 before reaching the coil 120.

In some embodiments, the inverter 144,145 can be a half bridge or full bridge induction heater. FIG. 2D is a circuit diagram of a full bridge induction heater which uses a resonant tank circuit to obtain a higher magnification of the current through the coil 120 than an inverter 144,145 without a resonant tank circuit could do alone. In another embodiment, the inverter 144, 145 may use a resonant tank circuit to obtain a magnification of the voltage when a series resonant tank circuit is used. The tank resonant circuit can be a series resonant tank circuit or a parallel resonant circuit. In an embodiment, a parallel tank circuit as the one shown in FIG. 2D is used, which used a full bridge LCLR structure. Other possible structures include, but are not limited to a half bridge, push pull, or single ended varieties.

Figure 4:
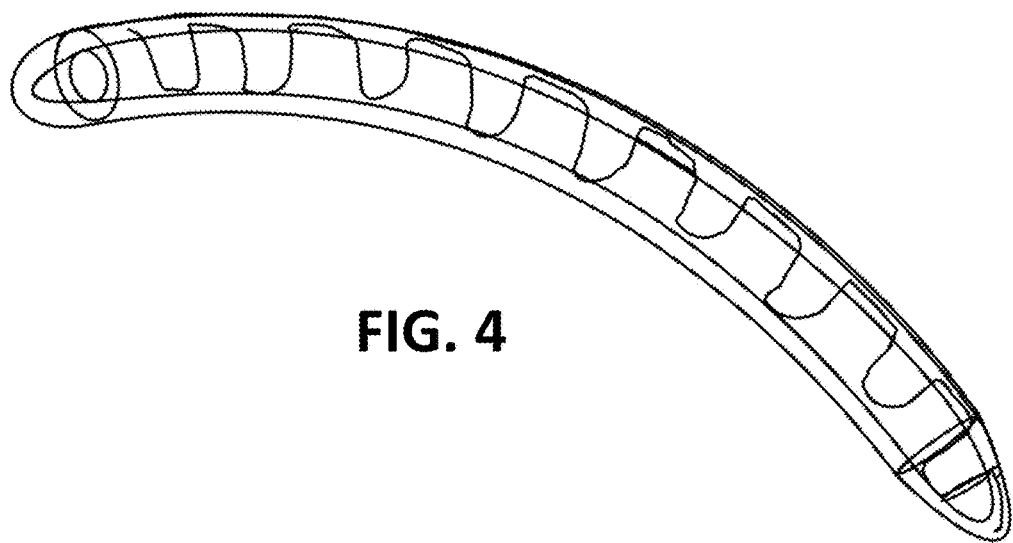
FIG. 4 is a side view of a penile prosthesis with a shape memory alloy having a spine and a rib configuration, according to aspects of the present disclosure.
Figure 5:
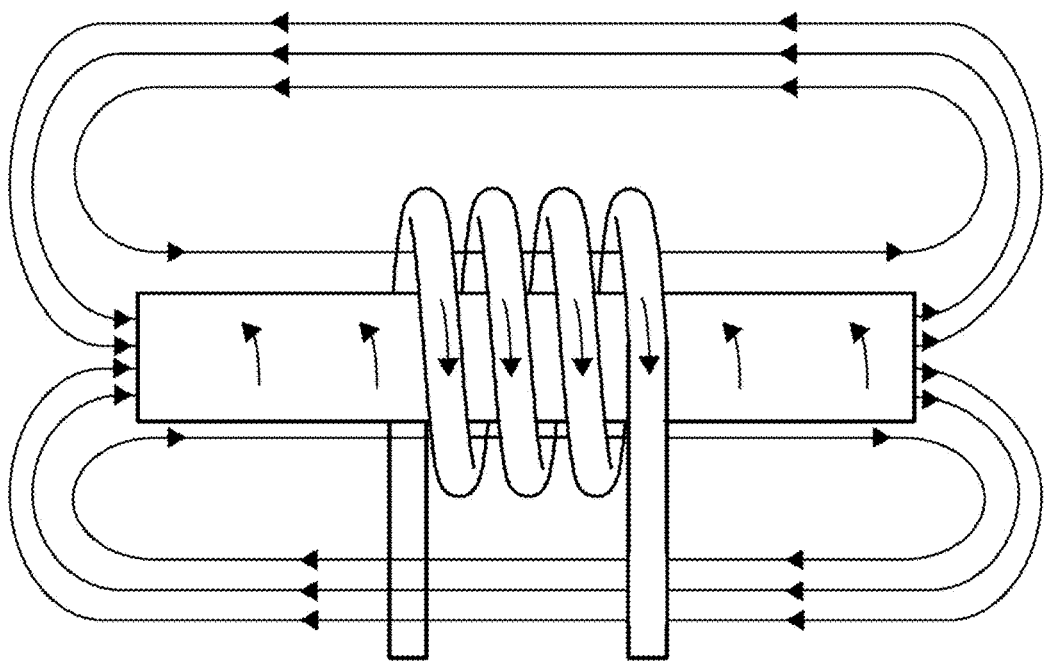
FIG. 5 is a sample magnetic induction on an elongated device, according to aspects of the present disclosure.

The current in the coil 120 generates an alternating magnetic field which induces eddy currents and generates heat in a penile prosthesis, as illustrated in FIG. 5. FIG. 4 is an illustration of a penile prosthesis, in one embodiment, which may be used with the magnetic induction apparatus 100 to create a magnetic induction system.

Figure 7:
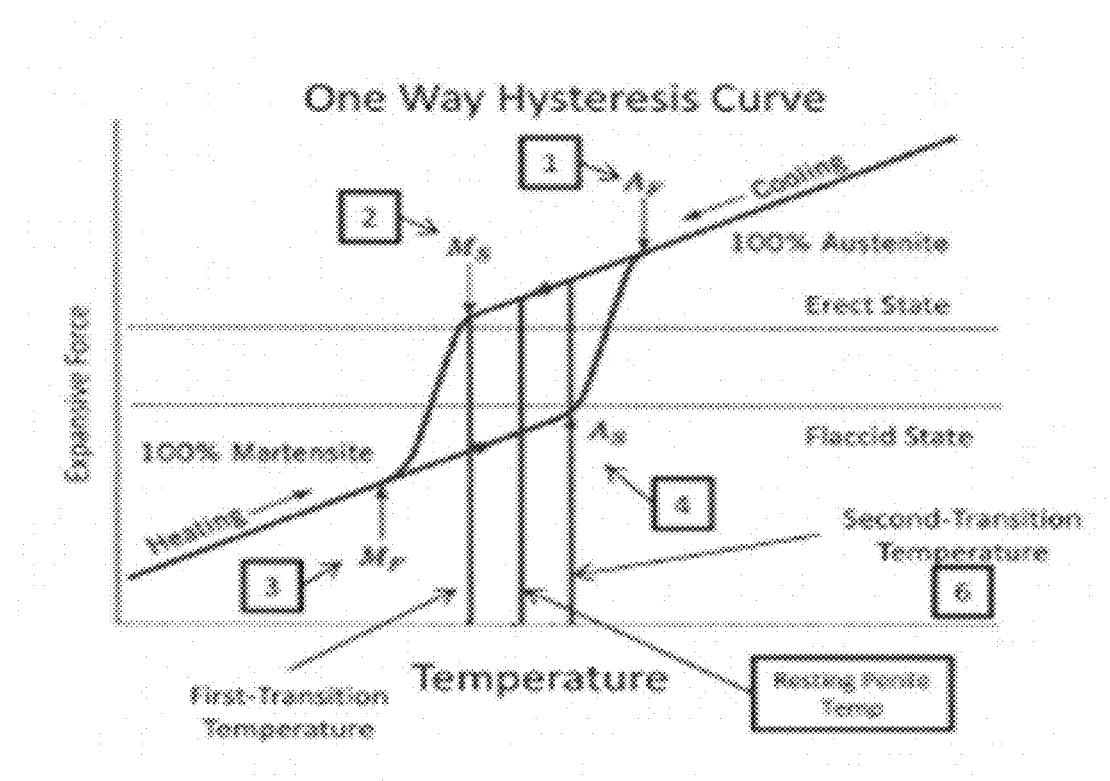
FIG. 7 is a hysteresis curve illustrating the transition temperature required to activate the shape memory alloy of the penile prosthesis from a flaccid state to an erect state, according to aspects of the present disclosure.

The magnetic induction apparatus 100 may increase the temperature of the shape memory alloy material of the penile prosthesis above a critical temperature to change the penile prosthesis from a flaccid state to an erect state. FIG. 7 is a hysteresis curve illustrating the transition temperature required to activate the shape memory alloy of the penile prosthesis from a flaccid state to an erect state. In an embodiment, the critical temperature may range from about 34° C. to about 46° C. This critical temperature range generally correlates to above the resting temperature of male genitalia that is about 34° C. and the temperature in which thermal pain receptors activate that is usually about 42-46° C. In various embodiments, the critical temperature may range from about 34° C. to about 36° C., from about 35° C. to about 37° C., from about 36° C. to about 38° C., from about 37° C. to about 39° C., from about 38° C. to about 40° C., from about 39° C. to about 41° C., from about 40° C. to about 42° C., from about 41° C. to about 43° C., from about 42° C. to about 44° C., from about 43° C. to about 45° C., and from about 44° C. to about 46° C. The penile prosthesis may need to be heated to between about 40° C. and 46° C. to transition the penile prosthesis from a flaccid state to a rigid state. In one embodiment, the critical temperature may be about 43° C.

The activation of the penile prosthesis from flaccid to erect may be stimulated by the magnetic induction apparatus 100 which may be power supplied with batteries, be engaged with the use of plug to a source of electrical power, or both. In case of the use of an AC supplier, in one embodiment, a rectifier 142 may be used to turn AC into DC power which would later be delivered to a frequency inverter 144. Currents at established frequencies may later be delivered to a coil 120 for generation of a variable electromagnetic field.

Non-limiting examples of the shape of the coil 120 of the magnetic induction apparatus 100 include a multi-turn helical coil 220 (FIG. 3A), a single-turn coil 320 (FIG. 3B), a split helical coil 420 (FIG. 3C), a pancake coil 520 (FIG. 3D), or any other shape capable of generating an electromagnetic field. Other shapes may include a flexible coil/pad which may take different shapes to adapt to the shape of the penis and/or may wrap around the penis. In some embodiments, the magnetic induction apparatus 100 may include a multi-turn coil with a sufficient number of turns to cover the entire area of the penile prosthesis. In other embodiments, the magnetic induction apparatus 100 may include a single turn coil or of a multi-turn coil with a limited number of turns compared to the penile prosthesis length. Depending on the coil design, the quantity of energy that the coil 120, 220, 320, 420, and 520 needs to transmit to the penile prosthesis in order to increase the temperature to the critical temperature varies significantly. In an embodiment, the multi-turn helical coil 220 has the capability to focus more of the magnetic flux. Therefore, the multi-turn helical coil 220 may be more efficient than other coil shapes from a thermodynamic point of view.

Coils 120, 220, 320, 420, and 520 with the current are isolated from direct contact with the skin during use of the magnetic induction apparatus 100. In an embodiment, the coil 120, 220, 320, 420, and 520 may be covered with a thermal and electrical insulant such as a silicon rubber, hypoxia, fiber glass, PTFE, or combinations thereof. In an embodiment, the thermal and electrical insulant may be embedded within the coil 120, 220, 320, 420, and 520. The cover may have a high melting point. In various aspects, the melting point of the cover may be at least about 150° C., at least about 200° C., at least about 250° C., or at least about 300° C. The electrical conductor material of the coil, pad, or other inducer in the magnetic induction apparatus 100 may be hollow and/or made of stranded litz wire in order to decrease the amount of heat dissipated by virtue of the skin effect. In one embodiment, the sheath 110 may act as the cover of the coils 120, 220, 320, 420, and 520 and may be composed of the insulant as described above.

In various embodiments, the magnetic induction apparatus 100 may be shaped as a sheath 110 with a center bore 130 for inserting the penis, as seen in FIG. 1. The penis with the penile prosthesis may be inserted in a "flaccid" state into the center bore 130 and the magnetic induction apparatus 100 is activated to allow the penile prosthesis to assume a "rigid" state and thus create a simulated erection such as shown in FIG. 1. The sheath may be compliant with the expanding geometry of the shape memory alloy penile prosthesis, allowing eddy currents to run in a close loop perpendicular to the variable magnetic field. The sheath 110 may take different shapes, such as having varying cross sections or thicknesses, as long as the penis with the penile prosthesis is able to fit within the bore 130 without contacting the sheath 110 The length of the sheath 110 may range from about 15 cm to about 30 cm long, from about 15 cm to about 20 cm, from about 20 cm to about 25 cm, and from about 25 cm to about 30 cm. The sheath 110 may have a bore 130 for the insertion of the penis with the penile prosthesis of at least about 4 cm diameter. In various embodiments, the sheath 110 may be available in a variety of lengths and bore diameters to provide for a user to have a magnetic induction apparatus 100 of an appropriate size. In various embodiments, the magnetic induction apparatus 100 may be rigid, flexible, or have a combination of rigid and flexible components. In an embodiment the magnetic induction apparatus 100 may be a wearable device.

Figure 6:
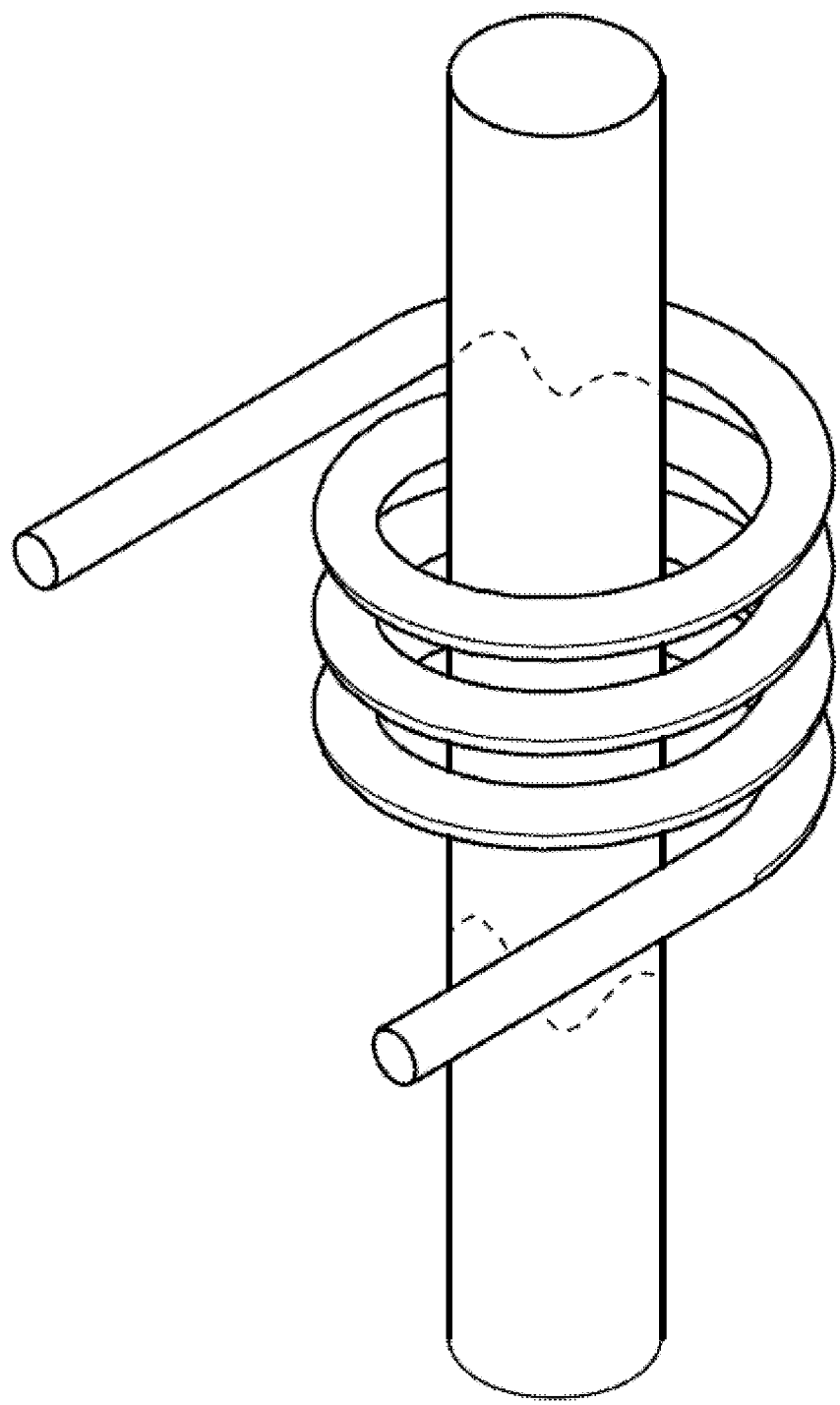
FIG. 6 is an elevated perspective view showing coils from a wand creating a source of heat on a section of the penile prosthesis, according to aspects of the present disclosure.

In other embodiments, the magnetic induction apparatus 100 may be linear or shaped like a "wand". The wand may be hand-held and moved over the penis shaft in a back and forth motion until the entire area of the penile prosthesis has been sufficiently covered to generate heat within the penile prosthesis. In one embodiment, the wand may generate heat on a portion of the penile prosthesis at a time, as illustrated in FIG. 6. The wand may include a handle portion so that the user can hold the apparatus without touching the coils 120, 220, 320, 420, and 520. The length of the wand may range from about 20 cm to about 50 cm, from about 20 cm to about 25 cm, from about 25 cm to about 30 cm, from about 30 cm to about 35 cm, from about 35 cm to about 40 cm, from about 40 cm to about 45 cm, and from about 45 cm to about 50 cm. The coils 120, 220, 320, 420, and 520 of the wand configuration may be only a portion of the wand length.

The magnetic induction apparatus 100 may include a means for measuring the temperature being imparted by the apparatus 100 and may be used for controlling the temperature of the penile prosthesis. This means for measuring the temperature may use a thermography diagnostic system. Such a diagnostic system may be used to determine when to terminate operation and cease heating the penile prosthesis as a safety mechanism. The magnetic induction apparatus 100 may also include pulse oximetry to measure increased oxygenation due to temperature increase in the penile prosthesis.

The activation frequency of the coils 120, 220, 320, 420, and 520 may vary between about 5 kHz and about 500 kHz. In general, a very high frequency for long duration (different seconds) of greater than about 200 kHz, usually gives a very intense fast and local heat pattern to the penile prosthesis. In order to obtain a more diffuse and slower heating effect with a deeper heat penetration, lower frequencies are advisable. In an embodiment, AC frequencies varying between 100 Hz and 50 kHz may be used to operate the magnetic induction apparatus 100. In various aspects, the AC frequency in the coils 120, 220, 320, 420, and 520 may vary from about 100 Hz to about 1000 Hz from about 500 Hz to about 1500 Hz, from about 1000 Hz to about 3000 Hz, from about 2000 Hz to about 4000 Hz, from about 3000 Hz to about 5000 Hz, from about 4000 Hz to about 6000 Hz, from about 5 kHz to about 15 kHz, from about 10 kHz to about to about 30 kHz, from about 20 kHz to about 40 kHz, and from about 30 kHz to about 50 kHz. When using AC frequencies, the amount of power of the magnetic induction apparatus 100 may be in the range of 5 W and 1500 W. In various embodiments, the power may range from about 5 W to about 50 W, from about 25 W to about 75 W, from about 50 W to about 100 W, from about 100 W to about 500 W, from about 250 W to about 750 W, from about 500 W to about 1000 W, from about 750 W to about 1250 W, and from about 1000 W to about 1500 W.

Depending on the coil shape, the magnetic field generated and its interaction with the penile prosthesis will change. For this reason, frequency and power and circuitry may be adapted to the coil 120, 220, 320, 420, and 520 with which it will be used. This is also critical for safety reasons. The amount of energy which the activator will need to provide to the penile prosthesis depends on the coil shape, the size/geometry of the shape memory alloy magnetic induction apparatus, the type of shape memory alloy material used, and the covering material on the magnetic induction apparatus and the penile prosthesis. These parameters may be used to determine the level of energy necessary for the required heat generation and the temperature increase may be limited.

The type of coil, the frequency of the activation, and the power used may affect the time needed to increase the temperature of the penile prosthesis to the desired critical temperature. In various embodiments, the time to reach the critical temperature may range from about 20 seconds to about 1 min, from about 20 seconds to about 40 seconds, from about 30 seconds to about 50 seconds, from about 40 seconds to about 1 min, from about 1 min to about 2 min, and about 2 min to about 3 min.

For example, in the sheath design of the magnetic induction apparatus 100 with a bore 130 of about 6 cm in diameter, a Nitinol penile prosthesis of about 18 cm of length, and an AC frequency of 10 kHz with sinusoidal shape, the magnetic induction apparatus 100 would need between about 60 W and 100 W to increase its temperature from 32° C. to 45° C. in a time between 30 and 40 seconds. In this example, the penile prosthesis includes two Nitinol exoskeletons (one for each corpora cavernosa of the penis) with diameter when fully expanded of 1.5 cm each. The electromagnetic field would bypass the tissues and any covers on the penile prosthesis and would directly affect the penile prosthesis. The use of a suitable magnetic flux concentrator may also be employed to alter the magnetic field direction in order to focus on specific parts of the penile prosthesis. To effect this alternate embodiment, non-limiting examples of materials include Alpha® Flux, Fluxtrol®, or a ferrite material.

In an alternative embodiment to low frequency alternating current, Radio Frequency (RF) levels of excitation may be used by the magnetic induction apparatus 100. The RF currents may be pulsed or continuous and may be applied for varying durations. Pulsed currents have the advantage to create lapsed times in the coil 120, 220, 320, 420, and 520 which may prevent the coil 120, 220, 320, 420, and 520 from overheating. Pulsed currents also allow the temperature of the penile prosthesis to decrease significantly during the elapsed times due to the SMA higher specific heat and lower thermal conductivity relative to materials such as copper which may be used for the coil 120, 220, 320, 420, and 520. In various embodiments, the duration of a pulsed RF current may range from about 3 seconds to about 20 seconds, from about 10 seconds to about 30 seconds, from about 20 seconds to about 40 seconds, from about 30 seconds to about 60 seconds, from about 45 seconds to about 75 seconds, from about 60 seconds to about 120 seconds, and from about 120 seconds to about 200 seconds. The duration of the single pulse applied to the coil may be between about 1 ms and 200 seconds.

The pulse rate may range between about 100 Hz and about 0.1 Hz. In various aspects, the pulse rate may range from about 0.1 Hz to about 1 Hz, from about 0.5 Hz to about 5 Hz, from about 1 Hz to about 10 Hz, from about 5 Hz to about 15 Hz, from about 10 Hz to about 30 Hz, from about 20 Hz to about 40 Hz, from about 30 Hz to about 50 Hz, from about 40 Hz to about 60 Hz, from about 50 Hz to about 70 Hz, from about 60 Hz to about 80 Hz, from about 70 Hz to about 90 Hz, and from about 80 Hz to about 100 Hz. The pulse lengths may be dependent on the size of the coil.

The penile prosthesis design may be implemented to improve inductive and non-inductive activation. One challenge with this design is Nitinol's or other shape memory alloy's lower level of heat conductivity compared to other metals such as iron, copper and aluminum that may be used in the coil 120, 220, 320, 420, and 520. The consequence of this difference means that heat is more concentrated in the area surrounded by the magnetic coil 120, 220, 320, 420, and 520. It is critical to have a distribution of heat along the penile prosthesis without concentration of extra-heat in one point (especially underneath the coil) and much lower temperatures in other areas.

Figure 11:
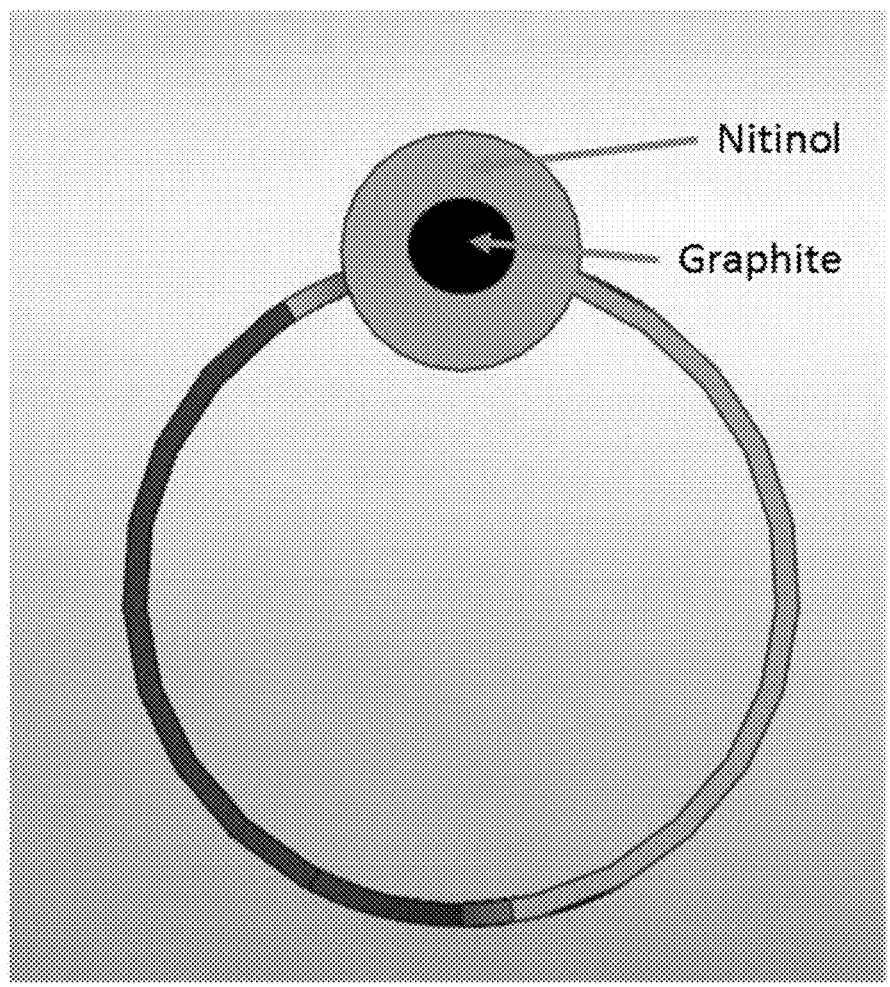
FIG. 11 is an illustration of one embodiment of a penile prosthesis with a grapheme internal core surrounded by Nitinol, according to aspects of the present disclosure.

In order to avoid heat concentration, a more conductive material may be added to the penile prosthesis in various embodiments. This material may be biocompatible and ferromagnetic or non-ferromagnetic. However, in order to maintain MRI compatibility non-ferromagnetic materials are preferred. Non-limiting examples of highly conductive materials for the prosthesis include gold, silver, graphene, graphite, and any other biocompatible, highly conductive, non-ferromagnetic materials. The association with the shape memory alloy can be multifold. The highly conductive material may be coated or plated on the shape memory alloy of the penile prosthesis both on the exterior surface and/or the interior surface of the penile prosthesis. The coating may be total or partial. In another embodiment, the penile prosthesis can be built in such a way that there is an external core of shape memory alloy and an internal core that is made of the highly conductive material in order to avoid galvanic coupling and cracking of the material during bending. FIG. 11 illustrates one embodiment of a penile prosthesis with a grapheme internal core surrounded by Nitinol. Techniques such as 3D printing or additive manufacturing techniques and material sintering may be used to this purpose. Alternatively, the penile prosthesis may include a highly conductive coating material. In an aspect, the highly conductive coating material may be applied using metallic spraying on the penile prosthesis or techniques such as plasma-enhanced chemical vapor deposition (PECVD). Optionally, conductive gels such MG Chemicals Super Thermal Grease or Thermal Silicone Grease Star922, can be pasted on the penile prosthesis facilitating the heat diffusion. Using these techniques, heat will be distributed for evenly without focalizing in the point directly associated with the proximity of the magnetic induction apparatus 100.

Also provided herein is a method for activating a penile prosthesis in a touchless manner. The method may include providing a penile prosthesis comprising a shape memory alloy, providing a magnetic induction apparatus 100 for inducing eddy currents to the penile prosthesis, and generating heat in the penile prosthesis to change the penile prosthesis from a flaccid state to a rigid state. The method may provide for a quicker, discrete, and more responsive means for heating a penile prosthesis and transforming it from a flaccid to an erect state.

EXAMPLES

Example 1

Magnetic Induction Testing

Figure 8:
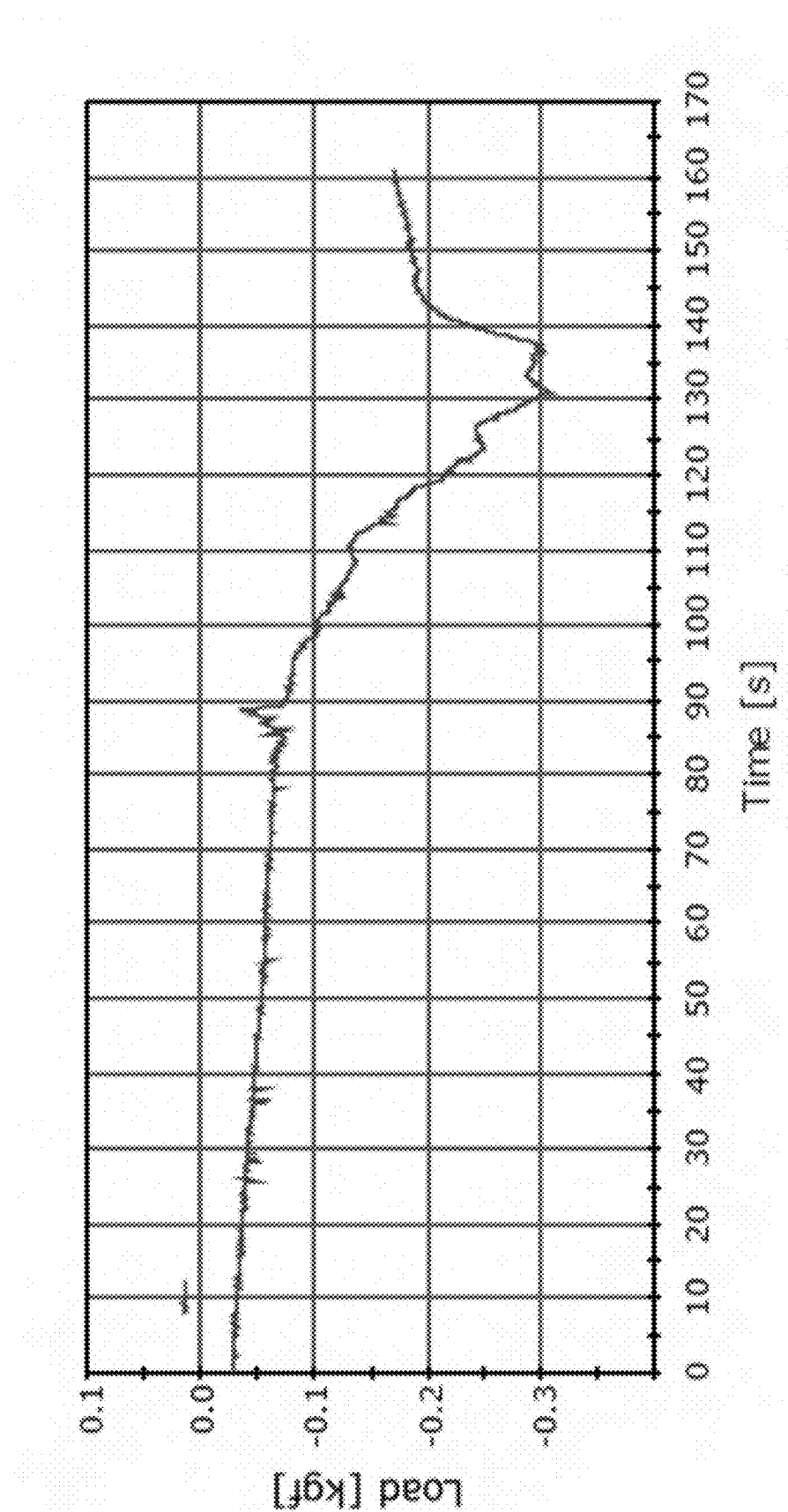
FIG. 8 is a graphical representation of the bending force of the penile prosthesis when activated to the erectile state through induction, according to aspects of the present disclosure.
Figure 9:
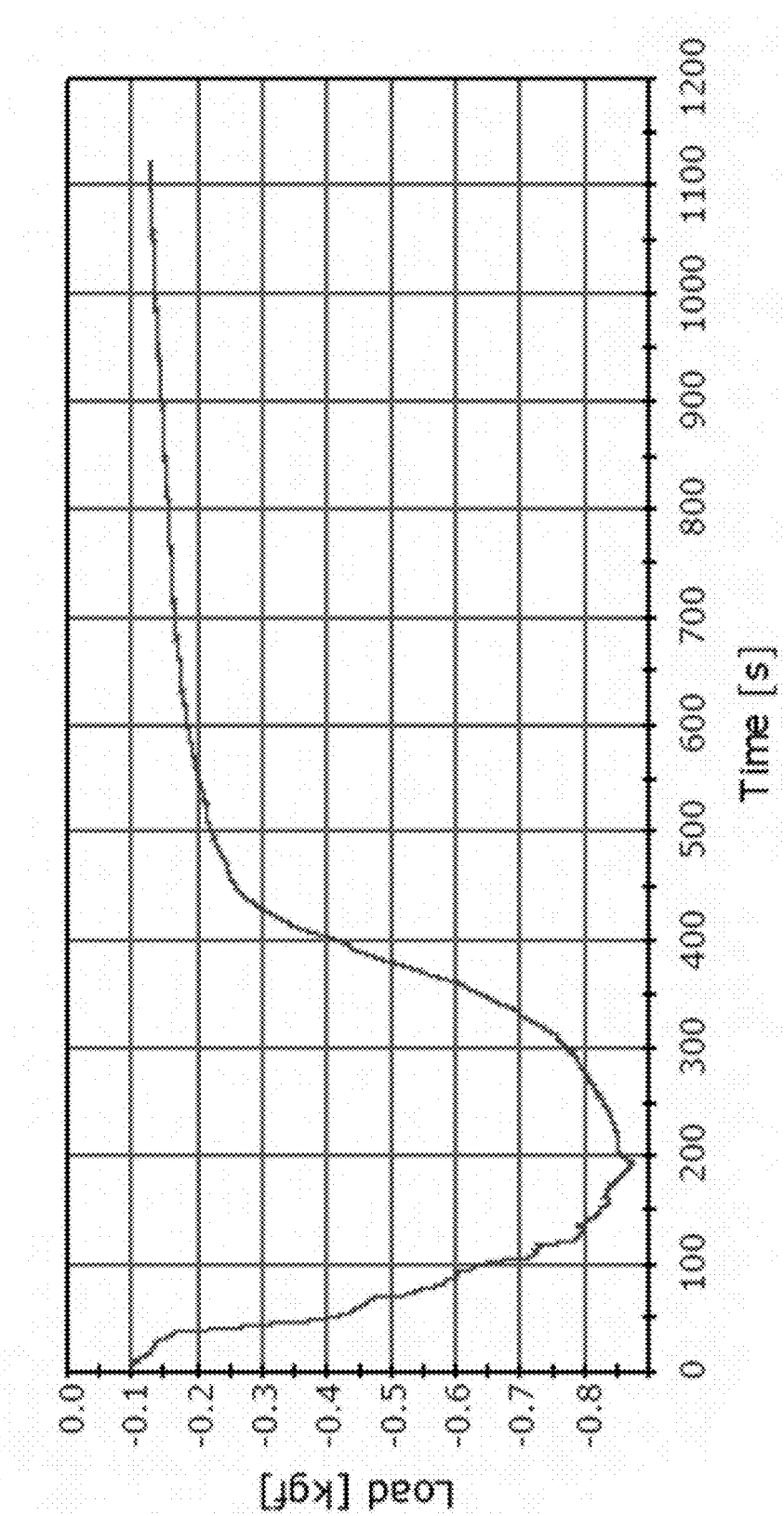
FIG. 9 is a graphical representation of the force generated by the penile prosthesis in the axial direction, according to aspects of the present disclosure.

In this example, prototypes of the magnetic induction apparatus were tested for activation. The activation speed, the temperatures and force generated by magnetic induction were measured with chronometers, thermocouples and testing machines. A penile prosthesis was placed in a vertical holder at ⅓ of their length with a preset deviation of 30 degrees. Using a mini-ductor II (Induction Innovations, Inc) of up to 1000 watts, a magnetic field was induced through the prosthesis. Once the prosthesis reached the erect configuration, the temperature and time to activation were measured. The recovery force generated in the perpendicular and in-axis plane during activation were then measured using a force measuring device (Instron Machine). The forces measured are illustrated in FIGS. 8 and 9.

Force was generated by the prosthesis in the axial direction. Table 1 summarizes the results for the force generated in the axial and lateral directions. Results shown by the shape memory alloy are compared to existing prostheses that are malleable and inflatable.

TABLE 1

|  | Axial Force | Lateral Force | Lateral Force Generated in expansion | Axial Force Generated in expansion |
| --- | --- | --- | --- | --- |
| Malleable | 6.65 kgf | 0.27 kgf | N/A | N/A |
| Inflatable | 1.42 kgf | 0.22 kgf | 0.16 kgf | 0.18 kgf |
| SMA (shape memory alloy) | 2.62 kgf | 0.30 kgf | 0.30 kgf | 0.95 kgf |

Using a handheld magnetic induction apparatus, the penile prosthesis was successfully activated with no direct contact. The time necessary to reach a straight/erect conformation using a 1000 watt magnetic inductor was 114±4.69 seconds. The force generated in the perpendicular plane as it transitioned from the flaccid to erect configuration was 0.3±0.015 kgf. The force generated in the axial plane was 0.95 kgf when measured at 30° angle. The final temperature reached by the prosthesis was 42±3° C. The use of a silastic covering generated no differences in activation times.

Figure 10:
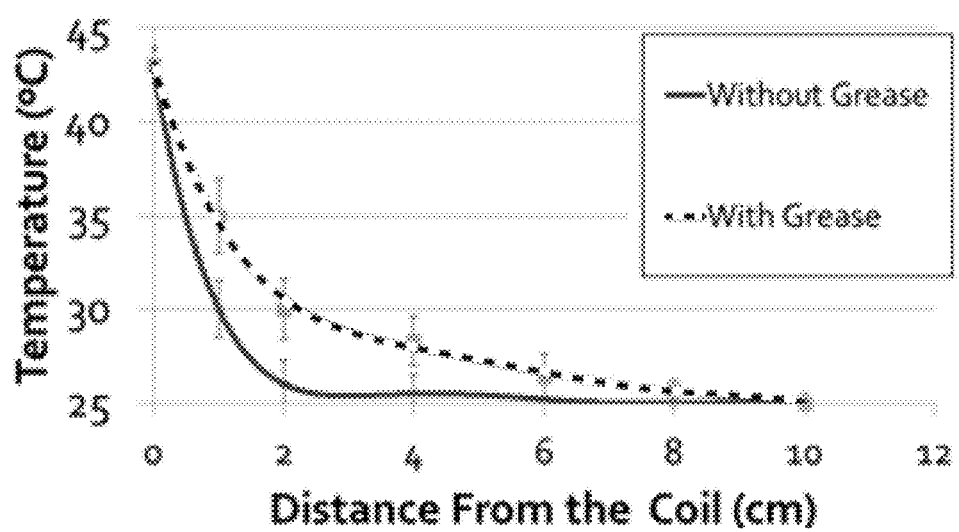
FIG. 10 is a graphical representation of the temperature of the penile prosthesis when heat was induced in a touchless manner with the wand at one end of the penile prosthesis using grease and not using grease, according to aspects of the present disclosure.

FIG. 10 shows the temperature of the penile prosthesis when heat was induced in a touchless manner with the wand at one end of the prosthesis. The use of the grease helps heat diffusion along the penile prosthesis accelerating the prosthesis phase change from a martensitic state and producing a simulated erection. This demonstrates that magnetic induction is a valid method to activate a shape memory alloy penile prosthesis.

While several particular embodiments of the present invention have been described herein, it will be appreciated by those skilled in the art that changes and modifications may be made thereto without departing from the invention in its broader aspects and as set forth in the following claims.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A magnetic induction apparatus for generating heat in a shape memory alloy penile prosthesis, the apparatus comprising:
   a power source for generating a current;
   a sheath having a length extending from a first end to a second end and comprising a bore configured to receive a penile prosthesis length, the bore extending the length of the sheath; and
   a multi-turn helical coil operatively connected to the power source for receiving the current, wherein the multi-turn helical coil surrounds the bore and extends the length of the sheath,
   wherein the length of the sheath is sufficient such that the bore and coils surround the entire penile prosthesis length, and
   wherein the current in the coil generates an alternating magnetic field which induces eddy currents and generates heat in the penile prosthesis to change the penile prosthesis from a flaccid state to a rigid state.

2. The magnetic induction apparatus of claim 1, wherein the coil is selected from the group consisting of a split helical coil and a flexible coil.

3. The magnetic induction apparatus of claim 1, further comprising a temperature sensor or a power sensor operatively connected to the multi-turn helical coil to measure the temperature or power at the coil, respectively.

4. The magnetic induction apparatus of claim 1, further comprising a thermal and electrical insulation that covers the coil selected from the group consisting of silicon rubber, fiber glass, PTFE, and combinations thereof.

5. The magnetic induction apparatus of claim 1, wherein the magnetic induction apparatus generates heat in the penile prosthesis, such that the penile prosthesis reaches a critical temperature.

6. The magnetic induction apparatus of claim 5, wherein the critical temperature is between 40° C. to 45° C.

7. The magnetic induction apparatus of claim 1, further comprising a rectifier in operable communication with a frequency inverter and the power source, wherein the current flows to the rectifier and frequency inverter before reaching the multi-turn helical coil.

8. The magnetic induction apparatus of claim 1, wherein the current is selected from a low frequency AC current and an RF current.

9. A magnetic induction system comprising:
   a penile prosthesis comprising a shape memory alloy and having a penile prosthesis length; and
   a magnetic induction apparatus comprising:
      a power source for generating a current;
      a sheath having a length extending from a first end to a second end and comprising a bore configured to receive the penile prosthesis, the bore extending the length of the sheath; and
      a multi-turn helical coil operatively connected to the power source for receiving the current, wherein the multi-turn helical coil surrounds the bore and extends the length of the sheath, and
   wherein the length of the sheath is sufficient such that the bore and coils surround the entire penile prosthesis length, and
   wherein the current in the coil generates an alternating magnetic field which induces eddy currents and generates heat in the shape memory alloy of the penile prosthesis to change the penile prosthesis from a flaccid state to a rigid state.

10. The magnetic induction system of claim 9, wherein the coil is selected from the group consisting of a split helical coil and a flexible coil.

11. The magnetic induction system of claim 9, wherein the penile prosthesis further comprises a conductive material selected from the group consisting of gold, silver, graphene, graphite, high conductive non-ferromagnetic materials, and combinations thereof.

12. A method for activating a penile prosthesis, the method comprising:
   providing a penile prosthesis comprising a shape memory alloy and having a penile prosthesis length;
   providing a magnetic induction apparatus comprising:
      a power source for generating a current;
      a sheath having a length extending from a first end to a second end and comprising a bore configured to receive the penile prosthesis, the bore extending the length of the sheath; and a multi-turn helical coil operatively connected to the power source for receiving the current, wherein the multi-turn helical coil surrounds the bore and extends the length of the sheath;

positioning the penile prosthesis within the bore of the magnetic induction apparatus such that the bore and coils surround the entire penile prosthesis length;

inducing eddy currents in the penile prosthesis using the magnetic induction apparatus; and generating heat in the penile prosthesis to change the penile prosthesis from a flaccid state to a rigid state.

13. The method of claim 12, wherein the magnetic induction apparatus heats the penile prosthesis to a critical temperature ranging from 40° C. to 45° C.

14. The method of claim 12, wherein the current is selected from a low frequency AC current and an RF current.

\* \* \* \* \*